United States Patent [19]

Sugasawa et al.

[11] Patent Number: 5,262,148

[45] Date of Patent: Nov. 16, 1993

[54] PROCESS FOR PREPARING BARIUM SULFATE

[75] Inventors: Hiroki Sugasawa; Satoshi Takano, both of Funabashi; Mikio Sakaguchi; Ichiro Sakamoto, both of Wakayama; Minoru Iwata, Matsudo; Nariyuki Kurotani, Chiba; Hideaki Koizumi, Tokyo; Hiroshi Itoh, Koganei; Risa Maejima, Kasukabe, all of Japan

[73] Assignee: KAO Corporation, Tokyo, Japan

[21] Appl. No.: 936,202

[22] Filed: Aug. 27, 1992

Related U.S. Application Data

[63] Continuation of Ser. No. 665,583, Mar. 6, 1991, Pat. No. 5,171,572.

[30] Foreign Application Priority Data

| Mar. 7, 1990 | [JP] | Japan | 2-55645 |
| Apr. 24, 1990 | [JP] | Japan | 2-108232 |
| Jun. 6, 1990 | [JP] | Japan | 2-147650 |
| Aug. 29, 1990 | [JP] | Japan | 2-227559 |
| Dec. 27, 1990 | [JP] | Japan | 2-414786 |

[51] Int. Cl.$^5$ ............................................. C01F 11/46
[52] U.S. Cl. ..................................... 423/554; 106/461; 106/471
[58] Field of Search ................ 424/402, 69; 106/461; 423/554

[56] References Cited

U.S. PATENT DOCUMENTS

| 4,272,296 | 6/1981 | Balducci et al. | 106/461 |
| 4,603,047 | 7/1986 | Watanabe et al. | 424/69 |
| 4,804,533 | 2/1989 | Imamura et al. | 424/69 |
| 4,894,093 | 1/1990 | Aderhold et al. | 106/461 |

FOREIGN PATENT DOCUMENTS 58-223617 12/1983 Japan.
61-129107 6/1986 Japan.

OTHER PUBLICATIONS

Ishii et al, Chemical Abstracts, vol. 112, No. 16, Apr. 16, 1990.

Primary Examiner—Thurman K. Page
Assistant Examiner—Raj Bawa
Attorney, Agent, or Firm—Oblon, Spivak, McClelland, Maier & Neustadt

[57] ABSTRACT

Barium sulfate having a specific crystal structure and optical characteristics is disclosed. The crystals have a plate-like structure of which the aspect ratio is 5–100 and the ratio of the square of the circumference of the plate and the area of the orthogonal projection plane is 20:1–150:1. In a preferred embodiment, a thin film of 25 μm thickness with 20% by weight of the barium sulfate powder concentration has a scattering transmittance of 70% or greater and a total transmittance of 85% or greater. The cosmetic compositions to which the barium sulfate is incorporated exhibits excellent extendibility and adhesion to the skin and can effectively hide the spots or freckles on the skin. The cosmetic composition satisfies both the fine naked skin feeling and the skin covering effect, which have never been satisfied by conventional cosmetic compositions.

1 Claim, 2 Drawing Sheets

PROCESS FOR PREPARING BARIUM SULFATE

This is a continuation of application Ser. No. 07/665,583, filed on Mar. 6, 1991, now U.S. Pat. No. 5,171,572.

BACKGROUND OF THE INVENTION

Field of the Invention

1. The present invention relates to a barium sulfate imparting an excellent transparent feeling to the bare skin and effectively hiding the freckles and spots on the skin and to a cosmetic composition comprising the barium sulfate.

2. Description of the Background Art

Barium sulfate is widely used as a shading material for the x-ray photography, a γ-ray absorber, a white pigment, and the like because of its characteristics unharmful to humans and its strong shielding capability. The applications of conventional barium sulfate to cosmetics, especially to foundation cosmetics, have been with some problems, such as its poor extendibility over the skin, inadequate adherence to the skin, insufficient transparency, and the inferior feeling to the bare skin which the conventional barium sulfate imparts after use.

In order to overcome these disadvantages of barium sulfate in the application to cosmetics, barium sulfate with a larger particle size (Japanese Patent Laid-open No. 41718/1983) and plate-like or needle-like barium sulfate crystals (Japanese Patent Laid-open (kokai) No. 174238/1987) have been proposed.

The production of such barium sulfate, however, involves complicated processes because of the requirement of a post-treatment of barium sulfate after synthesis, such as the treatment with heat or mineral acid. In addition, such a post-treatment develops the desired plate-like structure only insufficiently and the complete removal of crude barium sulfate after the post-treatment is difficult. There has been no barium sulfate which completely satisfied the requirements desired for the cosmetic material.

In view of this situation, the present inventors have undertaken extensive studies in order to develop barium sulfate satisfying the above-mentioned requirements. As a result, the inventors have found that barium sulfate (a) having a plate-like structure (defined more specifically below) and barium sulfate (A) having specific optical characteristics (defined more specifically below) exhibited excellent extendibility and adhesion to the skin, possessed high light-scattering and transparent characteristics, and could effectively hide the spots or freckles on the skin. These findings have led to the completion of the present invention.

SUMMARY OF THE INVENTION

Accordingly, an object of the present invention is to provide barium sulfate (a) having a plate-like crystal structure of which the aspect ratio is 5-100 and the ratio of the square of the circumference of the plate and the area of the orthogonal projection plane is 20:1-150:1.

Another object of the present invention is to provide barium sulfate (A) which, when made into a thin film with 20% by weight of powder concentration with a thickness of 25 μm, has a scattering transmittance (Haze) of 70% or greater and a total transmittance of 85% or greater.

Sill another object of the present invention is to provide a cosmetic composition comprising barium sulfate (a) or barium sulfate (A).

Other and further objects, features and advantages of this invention will appear more fully from the following description.

DETAILED DESCRIPTION OF THE INVENTION AND PREFERRED EMBODIMENTS

Figure 2:
FIG. 2 is a scanning electron microscope photograph showing the crystal structure of barium sulfate prepared by a conventional method of Comparative Example 3.
Figure 1:
FIG. 1 is a scanning electron microscope photograph showing the crystal structure of barium sulfate of the present invention prepared in Example 6.

Barium sulfate (a) of the present invention has a plate-like structure; it may be like a thin plate, a leaf, a petal, a foil, or a flake. The plate has an aspect ratio (average diameter of the plate/thickness) of 5-100, and a ratio of the square of the circumference of the plate and the area of the orthogonal projection plane of 20:1-150:1. As shown in FIG. 1, the crystal has a butterfly-like structure which has one or two mirror image planes perpendicular to the plate and a concave portion surrounding the periphery thereof.

If the aspect ratio is smaller than 5, the barium sulfate has a larger friction coefficient and gives an inferior feeling upon use. Barium sulfate having an aspect ratio exceeding 100 is difficult to produce. If the ratio of the square of the circumference of the plate to the area of the orthogonal projection plane is smaller than the defined range, the barium sulfate has a larger friction coefficient, whereas barium sulfate having a ratio greater than the above ratio is difficult to produce.

Figure 3:
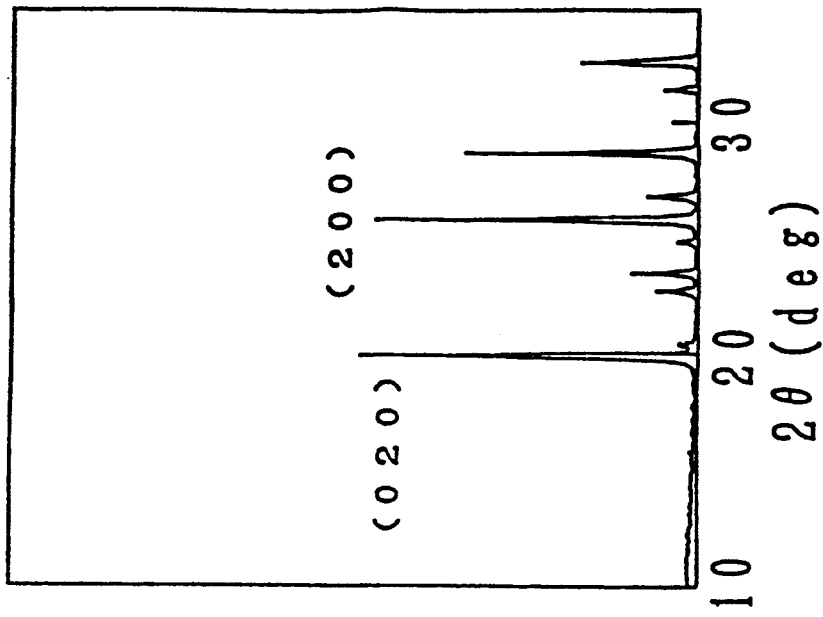
FIG. 3 is the x-ray diffraction pattern of plate-like barium sulfate of the present invention prepared in Example 6, showing the degree of the development on the (020) plane.
Figure 4:
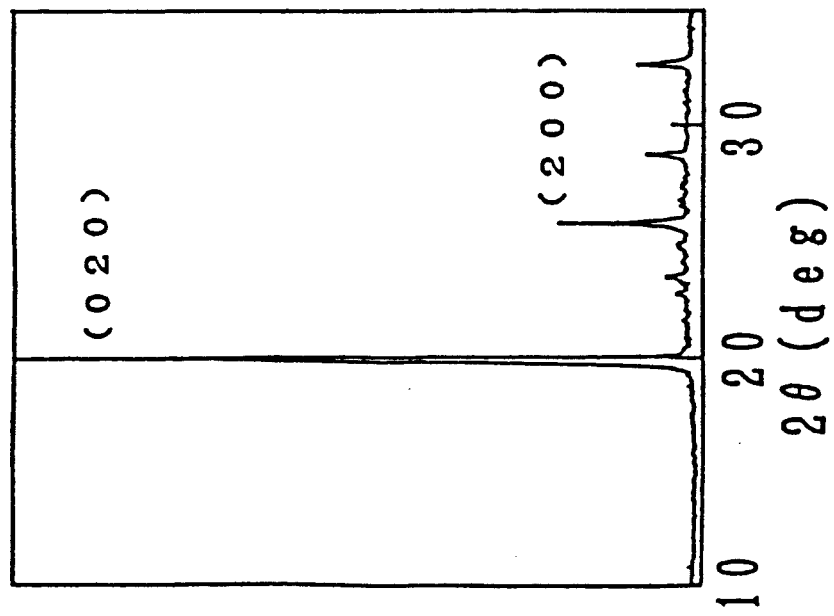
FIG. 4 is the x-ray diffraction pattern of barium sulfate of Comparative Example 3, showing the degree of the development on the (020) plane.

Another characteristic of barium sulfate (a) is its large ratio of intensity in the diffraction peaks on planes (020) and (200). As can be seen in FIG. 3, the ratio (020)/(200) is as large as 1.5-100.

Plate-like barium sulfate (a) of the present invention can be prepared by reacting a solution of a barium salt and a solution of a sulfate.

As a barium source, any barium salts which are dissolved in a solvent such as water or an alcohol can be used. Examples are barium chloride, barium nitrate, barium acetate, barium hydroxide, and the like. In order to give the excellent transparency which is characteristic to the barium sulfate of the present invention, the content of metallic ions other than barium in the barium source is preferably below 1,000 ppm.

In the present invention, "sulfate" is defined as a sulfate which is dissolved in a solvent such as water or an alcohol, and include sulfuric acid. Typical examples of sulfate are sodium sulfate, ammonium sulfate, and the like. Because of the same reason as applicable to the barium sources a solution of sulfate not containing metallic ions is preferable in view of the transparency of the product barium sulfate.

It is essential that the barium ion concentration in the solution of barium salt and the sulfate ion concentration in the solution of sulfate be both in the range of 0.001–0.05 mole/l. If the concentration is smaller than 0.001 mole/l, the structure of the crystals are more alike a column than a plate, resulting in an impaired feeling upon use of the product. In addition, the production yield of barium sulfate is decreased. If the concentration is greater than 0.05 mole/l, the structure of the crystals is very small particles rather than plate. Such a structure also impairs the feeling upon use of the product, and, in addition, the product exhibits a larger light scattering effect and poorer transparency.

The solution of barium salt and the solution of sulfate are mixed for reaction in such amounts that the molar ratio of barium and sulfate be 1:10–5:1. The reaction mixture is adjusted to pH 1.0–5.0 by an addition of hydrochloric acid, sulfuric acid, or nitric acid, as required. A preferable reaction temperature is 50–100° C., with an especially preferable temperature range being 60–95° C. The reaction at a pH or a temperature outside these ranges impairs the plate-like structure of crystals, which gives rise to poor transparency and an inadequate feeling of the barium sulfate upon use.

Barium sulfate (A) of the present invention has small reflection-scattered light because of its high total transmittance. On the other hand, its transmission scattered light is large due to its large dispersion transmittance. Because of this, the barium sulfate (A) has an effect of obscuring and hiding the underlying layer due to the scattering of the light passing through the powder, while exhibiting high transparency. Such an effect has not been seen in the conventional pigments, and the present inventors named it "distinctness-inhibiting effect".

Barium sulfate (A) of the present invention, when made into a thin film of 25 μm thickness with 20% by weight of concentration, has a scattering transmittance of 70% or greater and a total transmittance of 85% or greater. The effect of hiding colored spots in the underlying layer is not sufficient at a scattering transmittance below 70% while the transparency is not satisfactory at a total transmittance below 85%.

There are no specific limitations as to the structure of barium sulfate (A) of the present invention, so long as the same has the above-mentioned optical characteristics. An especially preferable embodiment of barium sulfate (A) is barium sulfate (a) of which the crystal structure is plate-like having the aspect ratio is 5–100 and the ratio of the square of the circumference of the plate and the area of the orthogonal projection plane is 20:1–150:1.

Plate-like barium sulfates (a) and (A) of the present invention can be incorporated in all make-up cosmetics such as foundations, face powders, face powder cakes, lipsticks, eye shadows, eye liners, and the like, and basic cosmetics such as creams, lotions, and the like. Such cosmetics may be in the form of a powder, cake, emulsion, oil, gel, or the like.

The amount of the barium sulfate to be incorporated into the cosmetics are arbitrarily determined depending the characteristics of the target cosmetics. A preferable amount is 0.1–100% by weight, with an especially preferable range being 10–99% by weight.

Cosmetic powders other than barium sulfate (a) or (A) can be used together in the cosmetic composition of the present invention. Especially preferable such cosmetic powders other than barium sulfate (a) or (A) which can further promote the feeling upon use, such as adherence and fitness to the skin, are (b) spherical powder and (c) a powdery pigment consisting of polyvalent metal salt of surface active agent. Preferable spherical powder (b) is that having an average volumetric accumulative particle diameter of 0.1–2 μm, and especially preferably 0.1–1 μm. Typical examples of such spherical powders include various metal oxides such as spherical alumina, spherical silica, spherical zirconia, spherical titanium oxide, and spherical zinc oxide; various plastics such as polyester, polyethylene, polystyrene, methylmethacrylate resin, copolymer of styrene and acrylic acid, polypropylene, polyvinyl chloride, teflon, acrylic beads, polyolefin, and the like; silica-containing composite oxides; silicone resins; aluminum silicate; cellulose; and the like. Among these, organic spherical powders are particularly preferable from the aspect of promoting the feeling upon use.

In the cosmetic composition comprising barium sulfate (a) or (A) and spherical powder (b), the amount of barium sulfate (a) or (A) in the total cosmetic components are 0.1–99% by weight, preferably 10–90% by weight, and the amount of spherical powder (b) is 0.1–99% by weight, and preferably 2–20% by weight.

Among powdery pigment consisting of polyvalent metal salt of surface active agent (c) those having smaller and larger diameters of the ratio between 1:1–1:100 and a thickness equivalent to or smaller than ½ of the larger diameter are especially suitable for use in the present invention.

The smaller and larger diameters and the thickness of the powdery pigment consisting of polyvalent metal salt of surface active agent are determined based on the electron microscope observation and the average particle diameter is determined by using a laser diffraction particle diameter analyzer (SK Laser Micron Sizer: trademark, manufactured by Seishin Co., Ltd.).

Examples of powdery pigment consisting of polyvalent metal salt of surface active agent (c) satisfying the above requirements include powders of polyvalent metal salt of alkyl phosphate (e.g. zinc monoalkyl phosphate), powders of polyvalent metal salt of amide sulfonate (e.g. calcium N-lauroyltaurine sulfonate), powders of polyvalent metal salt of acrylated amino acid (e.g. calcium salt of N-lauroyltaurine), and the like.

Powders of polyvalent metal salt of alkyl phosphate such as zinc monoalkyl phosphate can be produced by the methods disclosed, for example, by Japanese Patent Laid-open (kokai) Nos. 248605/1985 and 229889/1986. From the aspect of the superior feeling upon use zinc, calcium, magnesium, barium, or strontium phosphate having an alkyl group of a carbon atom content of 8 or greater is preferable. Particularly preferable is zinc monoalkyl phosphate of which the major component is plate-like crystal particles. Such zinc monoalkyl phosphate can be prepared, for example, by the salt-exchange reaction of an alkali metal salt of monoalkyl phosphate (I) having the neutralization value of 0.8–1.2 and zinc salt (II), followed by adjustment of pH to 2–6,

wherein R is a linear or branched, saturated or unsaturated hydrocarbon group having 8-32 carbon atoms, X is zinc, Y is inorganic anion, and m and n are individually an integer corresponding to the valence of X and Y, respectively.

The neutralization value here is 0.0 when monoalkyl phosphate is not neutralized, 1.0 when monoalkyl phosphate is neutralized up to the first equivalent point, and 2.0 when mcnoalkyl phosphate is neutralized up to the second equivalent point. A preferable neutralization value of an alkaline salt of monoalkyl phosphate (I) is 0.8-1.2, and especially preferably 0.9-1.1.

Among linear or branched, saturated or unsaturated hydrocarbon groups having 8-32 carbon atoms which are represented by R in formula (I), preferable groups are octyl, nonyl, decyl, dodecyl, undecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, and the like. In order for the shape and size of the particles of zinc monoalkyl phosphate to exhibit superior performance as a cosmetic powder, those having a linear saturated hydrocarbon group having 12-18 carbon atoms are especially preferable.

An alkali metal salt of monoalkyl phosphate (I) which is used as a raw material can be prepared by the neutralization of monoalkyl phosphate (I) by an alkali hydroxide or by the cation exchange of a dialkali metal salt using an ion-exchange resin or an acid. The purity of the monoalkyl phosphate which is used in the manufacture of the alkali metal salt of monoalkyl phosphate affects the crystal structure of an alkali metal salt of zinc monoalkyl phosphate, and this, in turn, greatly affect its characteristics as a cosmetic powder. Because of this reason, the purity of the monoalkyl phosphate which is used as the raw material is preferably 80% or greater, and especially preferably 95% or greater.

Y in formula (II) is an inorganic or organic anion, typified by inorganic anions such as halogen, $SO_4$, $NO_3$, $CO_3$, $PO_4$, and OH, and organic anions such as acetic acid, propionic acid, citric acid, and the like. Of these, especially preferable are inorganic anions such as halogen, $SO_4$, $PO_4$, $NO_3$, and $CO_3$, and ideal compounds of formula (II) are zinc salts such as $ZnSO_4$ and $ZnCl_2$.

An alkali metal salt of monoalkyl phosphate (I) and zinc salt (II) are reacted preferably in water or a mixed solvent of water and water-miscible organic solvent at a temperature at which the alkali metal salt of monoalkyl phosphate (I) completely dissolves. Water-miscible organic solvents which can be used here may be acetone, methanol, ethanol, iso-propyl alcohol, n-propyl alcohol, n-butyl alcohol, tert-butyl alcohol, sec-butyl alcohol, ethylene glycol, diethylene glycol, acetonitrile, tetrahydrofuran, dioxane, dimethylformamide (DMF), dimethylsulfoxide (DMSO), and the like. They can be used either independently or in combination of two or more. Of the above organic solvents, especially preferable are acetone, methanol, ethanol, iso-propyl alcohol, and n-propyl alcohol. The reaction solvent may be either water alone or a mixture of water and one or more of the above-mentioned solvents. Especially preferable solvents are mixed solvents of water and a water-miscible organic solvent such as acetone, methanol, ethanol, iso-propyl alcohol, or n-propyl alcohol. The method by which water and the water-miscible solvent are mixed are not restricted. A non-water-miscible solvent which does not affect the reaction may be blended with the mixed solvent. There are no limitations as to the method of preparing the reaction solvent.

There are no specific restrictions as to the concentration of an alkali metal salt of monoalkyl phosphate (I). There may be, however, a case where the concentration greatly affects the particle size of zinc monoalkyl phosphate which is produced. Namely, the greater is the concentration of the alkali metal salt of monoalkyl phosphate (I) in the reaction system, does the average particle size of zinc monoalkyl phosphate tend to be smaller. A preferable concentration of alkali metal salt of monoalkyl phosphate is smaller than 70% in order to produce zinc monoalkyl phosphate having a particle size of 5-30 $\mu$ which imparts desired feeling upon use.

The amount of zinc salt of formula (II) to be added to the reaction system is 0.4 mole or greater, and preferably 0.4-0.6 mol, per 1 mole of alkali metal salt of monoalkyl phosphate (I). Either an aqueous solution or solid of zinc salt of formula (II) can be used. A higher concentration is preferable when the zinc salt is added as an aqueous solution from the aspect of higher productivity.

There are no specific restrictions as to the reaction temperature so long as monoalkyl phosphate (I) completely dissolves at the temperature. A preferable temperature is 70° C. or higher.

The pH of the reaction system when zinc salt (II) is added to an alkali salt of monoalkyl phosphate (I) is dependent on the concentration of the alkali salt of monoalkyl phosphate (I) and the temperature. When the concentration of the alkali salt of monoalkyl phosphate (I) is 10% or greater, the pH may be smaller than 2 at a temperature of 70°-80° C., and, in most cases, smaller than 1-5. When the temperature is 70°-80° C., zinc monoalkyl phosphate produced is a mixture of needle-like crystals and plate-like crystals at a pH of smaller than 2, and the most particles take irregular shapes at a pH of greater than 6. These particles imparts a greatly decreased feeling upon use. It is essential in order to produce plate-like particles of zinc monoalkyl phosphate and to give an improved characteristics as a cosmetic powder to adjust the pH of the reaction system to 2-6, and preferably 3-5. The pH adjustment can be performed by an addition of an alkali compound. The amount of the alkali compound to be added is usually 0.3-0.7 equivalent, and preferably 0.45-0.55 equivalent, to the amount of alkali metal salt of monoalkyl phosphate (I). An alkali metal hydroxide, especially sodium hydroxide or potassium hydroxide, is a preferable neutralization agent. The manner in which the pH is adjusted is not specifically limited. The pH may be either adjusted after the addition of zinc salt (II) or can be controlled while zinc salt (II) is being added. Specific examples of the method of adjusting the pH are the method in which the reaction is carried out by the addition of an alkali metal salt of monoalkyl phosphate (I) and zinc salt (II) while controlling the pH with the addition of alkali metal hydroxide; the method in which all amount of zinc salt (II) is added to the alkali salt of monoalkyl phosphate (I) and then the pH is adjusted by the addition of alkali metal hydroxide; and the like.

The reaction mixture is then cooled, filtered, washed with water, and dried to obtain zinc monoalkyl phosphate containing plate-like crystals as a major component possessing excellent characteristics as a cosmetic powder.

Powders of polyvalent metal salt of amide sulfonate, such as calcium N-lauroyltaurin, can be prepared, for example, according to the same method as the method of producing conventional metal soaps. For example, a solution of a water soluble polyvalent metal salt is added to a solution of a water soluble metal salt of amide sulfonic acid of the formula,

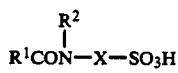

(wherein $R^1$ is a linear or branched alkyl, alkenyl, or hydroxyalkyl group having 7-12 carbon atoms, $R^2$ is a hydrogen atom or a methyl group, and X is an ethylene or propylene group, or a group $—CH_2CH(OH)CH_2—$), in such amounts that the water soluble polyvalent metal salt and the water soluble metal salt of amide sulfonic acid be equivalent, to effect the salt exchange, followed by stirring, filtration, washing with water, and drying. Aluminum sulfate, aluminum chloride, aluminum nitrate, potassium aluminum sulfate, magnesium chloride, magnesium nitrate, magnesium sulfate, potassium magnesium sulfate, calcium chloride, zinc chloride, zinc nitrate, zinc sulfate, zinc acetate, zirconium sulfate, zirconium chloride, titanium oxysulfate, titanium tetrachloride, and the like are given as examples of water soluble polyvalent metal salts.

The longer the time over which the water soluble polyvalent metal salt is added, the larger is the particle size of polyvalent metal salt of amide sulfonic acid which is produced.

Crystals of the polyvalent metal salt of amide sulfonic acid thus produced are ascicular, strip-like, or plate-like depending on the reaction conditions and the kind of the salt used. The plate-like crystals are especially preferable to be incorporated into the cosmetic composition because of the superior feeling upon use which it can provide.

A polyvalent metal salt of acylated amino acid, such as calcium salt of N-lauroyl-β-alanine, can also be prepared according to the same method as the method of producing conventional metal soaps. For example, a solution of a water soluble polyvalent metal salt is added to a solution of a water soluble metal salt of acylated amino acid of the formula,

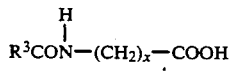

(wherein $R^3$ is a linear or branched alkyl, alkenyl, or hydroxyalkyl group having 7-21 carbon atoms and x is an integer of 1, 2, 3, 5, 10, or 11), in such amounts that the water soluble polyvalent metal salt and the water soluble metal salt of acylated amino acid be approximately equivalent, to effect the salt exchange, followed by stirring, filtration, washing with water, and drying. The same water soluble polyvalent metal salts given above relating to the production of the polyvalent metal salt of amide sulfonic acid can be used here.

The longer the time over which the water soluble polyvalent metal salt is added, the larger is the particle size of polyvalent metal salt of acylated amino acid which is produced.

Crystals of the polyvalent metal salt of acylated amino acid thus produced are ascicular, stripe-like, or plate-like depending on the reaction conditions and the kind of salt used. The plate-like crystals are especially preferable to be incorporated into the cosmetic composition because of the superior feeling upon use which it can provide.

There are no specific limitations as to the particle size of these powdery pigment consisting of polyvalent metal salt of surface active agent (c), although a preferable range of the average particle size is 0.1-50 μm.

The powdery pigment consisting of polyvalent metal salt of surface active agent (c) can be incorporated into the cosmetic composition as is, or after having been surface-treated with an inorganic compound such as silica, alumina, silica-alumina, titania, or barium sulfate; or with organic compound such as silicone, metallic soap, amino acid, lecithin, collagen, fluorine-containing resin, or the like.

The amount of barium sulfate (a) or (A) and powdery pigment consisting of polyvalent metal salt of surface active agent (c) to be incorporated into the cosmetic composition is not specifically limited. Usually, each component is added in an amount of 1-80% by weight, preferably 5-70% by weight, based on the total amount of the cosmetic composition. A preferable sum of the amounts of components (a) and/or (A), plus (c) in the cosmetic composition is 5-99% by weight, with the especially preferable range being 20-99% by weight.

Various components which are commonly used for cosmetics, other than components (a, (A), (b), and (c), may optional be added to the cosmetic composition of the present invention in an amount not to damage the effect intended by the present invention. Such optional components include various oils, surfactants, powders other than powder components (a), (A), (b), and (c), water soluble polymers, preservatives, medicines, pigments, perfumes, UV absorbers, humectants, dyes, water, and the like. Examples of oils which can be used are liquid paraffin, petroleum, paraffin wax, squalan, bees wax, carnauba wax, olive oil, lanolin, fatty acid, higher alcohol, synthetic ester oils obtained by reacting a fatty acid and a higher alcohol, and the like. Examples of surfactants include nonionic surface active agents such as polyoxyethylene alkyl ethers, polyoxyethylene fatty acid esters, polyoxyethylene sorbitan fatty acid esters, glycerol fatty acid esters, polyglycerol fatty acid esters, polyoxyethylene glycerol fatty acid esters, polyoxyethylene hydrogenated castor oil, polyoxyethylene sorbitol fatty acid esters, and the like; anionic surface active agents typified by fatty acid soaps such as sodium stearate, triethanolamine palmitate, and the like; cationic surface active agents; and amphoteric surface active agents. Given as examples of water soluble polymers are various commonly used water soluble polymers such as carboxymethyl cellulose, methyl cellulose, hydroxymethyl cellulose, polyvinyl alcohol, polyvinyl pyrrolidone, taragacanth gum, carrageenan, locust been gum, dextrin, dextrin fatty acid esters, carboxyvinyl polymer, xanthan gum, gelatin, sodium alginate, gum arabica, and the like. Examples of humectants are sorbitol, xylitol, glycerol, maltitol, propylene glycol, 1,3-butylene glycol, 1,4-butylene glycol, sodium pyrrolidone carboxylate, lactic acid, sodium lactate, polyethylene glycol, and the like. As examples of preservatives, p-oxybenzoic acid alkyl esters, sodium benzoate, potassium sorbate, and the like are given. Various medical components which are commonly used in cosmetics, such as vitamins, Chinese medicines, analgesics, antiphlogistics, germicides, and the like, can be incorporated to the cosmetic composition of the present invention. Cosmetic powders other than the essential powder components (a), (A), (b), and (c) are, for example, inorganic powders such as talc, mica, kaolin, cerisite, potashmica, synthetic mica, phlogopite, lepidolite, biotite, lithia mica, vermiculite, magnesium carbonate, calcium carbonate, diatomaceous earth, magnesium silicate, calcium silicate, aluminum silicate, barium silicate, strontium silicate, metallic tangstenate, hydroxy apatite, hydrous silicic acid, anhydrous silicic acid, magnesium oxide, bentonite, zeolite, ceramic powders, aluminum hydroxide, and the like; organic powders such as nylon powder, polyethylene powder, polymethylbenzoguanamine powder, polymethyl methacrylate powder, polytetrafluoroethylene powder, microcrystalline cellulose powder, rice starch, lauroyl lysine, and the like; color pigments such as titanium oxide, zinc oxide, zirconium oxide, red iron oxide, iron titanate, iron hydroxide, loess, black iron oxide, carbon black, mango violet, cobalt violet, chromium oxide, chromium hydroxide, cobalt titanium, ultramarine blue, iron blue, and the like; pearling pigments such as titanium oxide-coated mica, titanium oxide-coated bismuth oxychloride, bismuth oxychloride, titanium oxide-coated talc, fish scales, colored titanium oxide-coated mica, and the like; and metallic powder pigments such as aluminum powder, stainless steel powder, copper powder, and the like. Given as examples of dyes are tar-derived dyestuffs such as Erythrosine (CI No. 45430), Phloxine B (CI No. 45410), Acid red (CI No. 45100), Lithol rubine B (CI No. 15850), Lithol rubine BCA (CI No. 15850), Lake red CBA (CI No. 15585), Lithol red (CI No. 15630), Deep maroon (CI No. 15880), Tetrabromofluorescein (CI No. 45380), Helidone pink CN (CI No. 73360], Fast acid magenta (CI No. 17200), Parmatone red (CI No. 12085), Eosine YS (CI No. 45380), Violamine R (CI No. 45190), Oil red XO (CI No. 12140), Tartrazine (CI No. 19140), Sunset yellow FCF (CI No. 15985), Vranine (CI No. 45350), Quinoline yellow WS (CI No. 47005), Quinoline yellow SS (CI No. 47000), Hanza yellow (CI No. 11680), Brilliant blue FCF (CI No. 42090), Indigo caramine (CI No. 73015), Indigo (CI No. 73000), Phtalocyanine blue (CI No. 74160), Fast green FCF (CI No. 42053), Alizanine cyanine green F (CI No. 61570), Pyranine conc (CI No. 59040), Light green SF yellowish (CI No. 42095), Dibromofluorescein (CI No. 45370), Parmanent orange (CI No. 12075), Parmanent orange G (CI No. 21110), Diiodofluorescein (CI No. 45425A), Erythrosine yellowish NA (CI No. 45425), and the like; organic pigment powders such as carminic acid, laccaic acid, brazilin, carcumin, crocin, and the like; and lake pigment powders such as zirconia lake, barium lake, aluminum lake, and the like. UV absorbers which can be used include p-aminobenzoic acid compounds, anthranilic acid compounds, salicylic acid compounds, cinnamic acid compounds, benzophenone compounds, and the like.

The cosmetic composition of the present invention can be prepared by blending the above components according to a conventional method.

Other features of the invention will become apparent in the course of the following description of the exemplary embodiments which are given for illustration of the invention and are not intended to be limiting thereof.

EXAMPLES

In the Examples Comparative and Examples below the feeling upon use, transparency, and the degree of the development of plate-like crystal structure are evaluated according to the following methods.

Feeling upon use

One (1) gm of a sample of barium sulfate powder was held between 2 discs with a diameter of 50 mmΦ and a thickness of 10 mm to which a sheet of artificial skin is attached. While applying the perpendicular load of 50 gf, one of the discs was rotated at a rate of 300 rpm and the torque (F) was measured on the another disc to determine the friction coefficient (F/50) of the powder.

Transparency

Twenty percent (20%) by weight of barium sulfate powder was added to silicone oil which is a dispersing medium. The mixture was homogeneous kneaded and applied to a glass plate using an applicator to produce a thin film of 25 $\mu$m thickness. The transmittance of the thin film was measured by a Haze & Reflecto meter (type HR-100: trademark, product of Murakami Color Research Laboratory).

The development of plate-like crystal structure

One (1) gm of barium sulfate powder was dispersed in 50 cc of ethanol. A thin film with a thickness of 15 $\mu$m was formed on a glass plate using the barium sulfate dispersion and the film was dried. The ratio of diffraction peaks (020)/(200) of the barium sulfate crystals was determined by an x-ray diffraction using x-ray diffractometer (type RAD-200: trademark, manufactured by Rikagaku Electric Co.) irradiating CuK $\alpha$-ray at 40 kV and 80 mV.

EXAMPLE 1

Aqueous solutions of barium chloride (0.008 mol/1) and sulfuric acid (0.005 mol/1) were prepared by dissolving 1.974 gm of barium chloride (special reagent grade) and 0.505 gm of sulfuric acid (special reagent grade) into 1,000 gm of ion-exchanged water. Each solution was heated at 70° C. The barium chloride solution was added dropwise over a period of 10 minutes to the sulfuric acid solution, while the latter was stirred at 1,000 rpm by a U-shaped blade. After the addition, the mixture was stirred for a further 3 minutes to complete the reaction. The mixture was kept at pH 3.5 during the reaction. After cooling to the room temperature, the reaction mixture was filtered through a 5C filter paper, washed with water, and dried at 105° C. for 2 hours to obtain 1.12 gm of barium sulfate powder.

The powder had an average plate diameter of 5.3 $\mu$m, aspect ratio of 58, and a ratio of the square of the circumference of the plate and the area of the orthogonal projection plane of 88:1. X-ray diffraction revealed that the crystal of barium sulfate had a ratio of the diffraction peaks on planes (020) and (200) of 5.3. The crystals had a butterfly-like shape with a well-developed plate-like structure. The powder was transparent and felt slippery.

When incorporated into a foundation composition, the powder exhibited a better feeling upon use and produced more transparent cosmetic films than foundations to which conventional body powders such as mica and talc are incorporated.

EXAMPLE 2

Aqueous solutions of barium acetate (0.02 mol/1) and sodium sulfate (0.02 mol/1) were prepared by dissolving 11.043 gm of barium acetate (special reagent grade) and 2.926 gm of sodium sulfate (special reagent grade) each into 2,000 gm of ion-exchanged water.

Each solution was heated at 85°C. Then, 6.53 gm of barium sulfate powder was obtained in the same manner as in Example 1.

The powder had an average plate diameter of 7.2 μm, aspect ratio of 68, and a ratio of the square of the circumference of the plate and the area of the orthogonal projection plane of 78:1. X-ray diffraction revealed that the crystal of barium sulfate had a ratio of the diffraction peaks on planes (020) and (200) of 5.3. The crystals had a butterfly-like shape with a well-developed plate-like structure. The powder was transparent and felt slippery.

When incorporated into a foundation composition, the powder exhibited a better feeling upon use and produced more transparent cosmetic films than foundations to which conventional body powders such as mica and talc are incorporated.

EXAMPLE 3

Aqueous solutions of barium acetate (0.02 mol/1) and sodium sulfate (0.02mol/1) were prepared by dissolving 11.043 gm of barium acetate (special reagent grade) and 2.926 gm of sodium sulfate (special reagent grade) into 2,000 gm of ion-exchanged water. The two solutions were heated at 85° C. and mixed together. The mixture was adjusted to pH 3.0 by an addition of 5.3 cc of concentrated hydrochloric acid, followed by the reaction in the same manner as in Example 1 to obtain 6.53 gm of barium sulfate powder.

The powder had an average plate diameter of 8.3 μm, aspect ratio of 77, and a ratio of the square of the circumference of the plate and the area of the orthogonal projection plane of 88:1. X-ray diffraction revealed that the crystals of barium sulfate had a ratio of the diffraction peaks on planes (020) and (200) of 16.8. The crystals had a butterfly-like shape with a well-developed plate-like structure. The powder was transparent and slippery.

When incorporated into a foundation composition, the powder exhibited a better feeling upon use and produced more transparent cosmetic films than foundations to which conventional body powders such as mica and talc are incorporated.

COMPARATIVE EXAMPLE 1

Aqueous solutions of barium chloride (0.1 mol/1) and sulfuric acid (0.1 mol/1) were prepared by dissolving 24.675 gm of barium chloride (special reagent grade) and 10.100 gm of sulfuric acid (special reagent grade) into 1,000 gm of ion-exchanged water. The two solutions were heated at 30° C., followed by the reaction in the same manner as in Example 1 to obtain 19.5 gm of barium sulfate powder.

The powder had an average plate diameter of 0.3 μm, aspect ratio of 1.5, and a ratio of the square of the circumference of the plate and the area of the orthogonal projection plane of 78:1. X-ray diffraction revealed that the crystal of barium sulfate had a ratio of the diffraction peaks on planes (020) and (200) of 1.0. The product was fine powder and its plate-like structure was not sufficiently developed. The powder was not transparent nor felt slippery.

COMPARATIVE EXAMPLE 2

Aqueous solutions of barium chloride (0.1 mol/1) and sulfuric acid (0.1 mol/1) were prepared by dissolving 24.675 gm of barium chloride (special reagent grade) and 10.100 gm of sulfuric acid (special reagent grade) into 1,000 gm of ion-exchanged water. The two solutions were heated at 30° C., followed by the reaction in the same manner as in Example 1 at pH 5.8 to obtain 19.5 gm of barium sulfate powder.

The powder had an average plate diameter of 6.3 μm, aspect ratio of 3.5, and a ratio of the square of the plate circumference and the area of the orthogonal projection plane of 18:1. X-ray diffraction revealed that the crystal of barium sulfate had a ratio of the diffraction peaks on planes (020) and (200) of 1.3. The crystals were of deformed plate-like shapes with an insufficiently developed plate structure. The powder was not transparent nor felt slippery.

EXAMPLE 4

Aqueous solutions of barium chloride (0.050 mol/1) and sulfuric acid (0.05 mol/1were mixed at 1:1 molar ratio and reacted at 70° C. to obtain plate-like barium sulfate crystals powder with a butterfly-like shape.

The average diameter, (circumference)$^2$/(the area of the orthogonal projection plane), and aspect ratio of the crystals were determined and shown in Table 1. The friction coefficient, the transmittance, and the ratio of x-ray diffraction peaks were determined, in order to evaluate the feeling upon use, the transparency, and the degree of the development of plate-like crystal structure. The results are shown in Table 1.

EXAMPLES 5-14 AND COMPARATIVE EXAMPLES 3-7

Barium sulfate powders of plate-like crystals were prepared in the same manner as in Example 1, except that concentrations of barium and sulfate sources, the blending ratios, and the reaction temperatures listed in Table 1 were employed. The reaction was carried out at pH 2.1-4.8.

The average diameter, (circumference)2 (the area of the orthogonal projection plane), and aspect ratio of the crystals were determined and shown in Table 1. In order to evaluate the feeling upon use, the transparency, and the degree of the development of plate-like crystal structure, the friction coefficient, the transmittance, and the ratio of x-ray diffraction peaks were determined. The results are shown in Table 1.

TABLE 1

| | Concentration (mol/l) | | Blending ratio | Reaction temperature | Crystals | | | Powder friction coefficient | Transparency (%) | Ratio of x-ray diffraction peaks *2 |
|---|---|---|---|---|---|---|---|---|---|---|
| | $Ba^{2+}$ | $SO_4^-$ | *1 | (°C.) | Average diameter (μm) | (circumference)$^2$/(the area) | Aspect ratio | | | |
| Example | | | | | | | | | | |
| No. 4 | 0.050 | 0.050 | 1/1 | 70 | 9.6 | 84 | 41 | 0.45 | 83.9 | 5.1 |
| No. 5 | 0.010 | 0.010 | 1/1 | 80 | 7.8 | 69 | 63 | 0.43 | 85.0 | 32.6 |
| No. 6 | 0.005 | 0.005 | 1/1 | 90 | 5.8 | 58 | 29 | 0.46 | 82.9 | 6.3 |
| No. 7 | 0.005 | 0.005 | 1/1 | 60 | 4.2 | 31 | 9 | 0.48 | 81.2 | 2.2 |
| No. 8 | 0.002 | 0.002 | 1/1 | 75 | 3.8 | 24 | 8 | 0.45 | 79.8 | 2.3 |
| No. 9 | 0.005 | 0.005 | 1/4 | 85 | 5.3 | 55 | 25 | 0.45 | 81.4 | 5.2 |

TABLE 1-continued

|  | Concentration (mol/l) | | Blending ratio *1 | Reaction temperature (°C.) | Crystals | | | Powder friction coefficient | Transparency (%) | Ratio of x-ray diffraction peaks *2 |
|---|---|---|---|---|---|---|---|---|---|---|
|  | $Ba^{2+}$ | $SO_4^-$ |  |  | Average diameter (μm) | (circumference)$^2$/ (the area) | Aspect ratio |  |  |  |
| No. 10 | 0.010 | 0.010 | 4/1 | 90 | 7.1 | 74 | 98 | 0.41 | 84.7 | 82.1 |
| No. 11 | 0.002 | 0.004 | 1/2 | 95 | 5.6 | 55 | 23 | 0.47 | 82.2 | 3.5 |
| No. 12 | 0.005 | 0.001 | 5/1 | 85 | 5.4 | 61 | 25 | 0.41 | 83.1 | 4.8 |
| No. 13 | 0.020 | 0.005 | 1/1 | 80 | 6.4 | 66 | 32 | 0.44 | 83.3 | 5.3 |
| No. 14 | 0.010 | 0.050 | 1/1 | 75 | 8.4 | 73 | 14 | 0.48 | 80.6 | 3.1 |
| Comparative Example |  |  |  |  |  |  |  |  |  |  |
| No. 3 *3 | — | — | — | — | 4.6 | — | — | 0.58 | 68.8 | 1.1 |
| No. 4 | 0.0005 | 0.0005 | 1/1 | 90 | 2.8 | — *4 | — *4 | 0.61 | 66.6 | 0.5 |
| No. 5 | 0.100 | 0.100 | 1/1 | 85 | 0.2 | — *5 | — *5 | 0.63 | 61.4 | 0.5 |
| No. 6 | 0.005 | 0.005 | 1/1 | 30 | 3.3 | — *6 | — *6 | 0.57 | 69.2 | 1.0 |
| No. 7 | 0.010 | 0.010 | 50/1 | 75 | 10.5 | — *7 | — *7 | 0.61 | 65.6 | 0.8 |

*1: Molar ratio (barium salt solution/sulfate solution)
*2: (020)/(200)
*3: Conventional barium sulfate
*4: Column-shaped
*5: Fine particles
*6: Irregular plate-like shape, could not measured.
*7: Deformed shape, could not measured.

TEST EXAMPLE 1

Powder samples listed in Table 2 were dispersed in dimethyl silicone oil (KF-96-1000CS: trademark, manufactured by Shin-etsu Chemical Co., Ltd.) at a concentration of 20% and kneaded by a Hoover muller in order to homogeneously disperse the powders in the silicone oil. The material was applied to a glass plate using a Baker applicator to produce a thin film with a thickness of 25 μm. Scattered transmittance (Haze; H=Tt/Td) of the film samples was determined by the measurement of the total transmittance (Tt) and dispersion transmittance (Td) using a Haze Reflecto meter HR-100 (trademark, manufactured by Murakami Color Research Laboratory). The results are given in Table 2.

TABLE 2

| Manufacturer | Pigments | Average diameter (μm) | Total transmission (%) | Scattered transmission (%) |
|---|---|---|---|---|
| Shokubai Kasei Kogyo | Silica Microbead P-1500 *1 | 5.00 | 93.30 | 24.40 |
| Shokubai Kasei Kogyo | Silica Microbead P-400 *1 | 1.60 | 93.40 | 17.30 |
| Tokuyama Soda | Spherical Ceramics S-03 *1 | 0.39 | 92.20 | 7.50 |
| Tokuyama Soda | Spherical Ceramics S-006 *1 | 0.52 | 93.00 | 13.15 |
| Iwatani Sangyo | E-8 *1 | 1.40 | 93.25 | 17.55 |
| Horie Kako | Sericite SP | 2-20 | 90.60 | 41.20 |
| Kakuhachi Fish Scale | Eight Pearl 300S *2 | 2-20 | 90.50 | 30.90 |
| Asda Powder Manf. | Talc JA46R | 2-20 | 90.50 | 30.90 |
| Yamaguchi Mica | Mica Y-2300 | 2-20 | 90.90 | 21.20 |
| Sakai Chemical | BARIFINE BF-20 *3 | 0.03 | 88.80 | 28.30 |
| Nihon Chemical | Precipitative Barium Sulfate ST | 0.80 | 66.60 | 85.40 |
| Sakai Chemical | Special Barium Sulfate | 4.20 | 87.60 | 36.70 |
| Nihon Chemical | Precipitative Barium Sulfate D-2 | 1.10 | 79.90 | 79.40 |
| Sakai Chemical | Plate-like Barium Sulfate | 5-10 | 91.10 | 43.80 |
| Nihon Chemical | Precipitative Barium Sulfate ST/Si | 1.15 | 88.10 | 64.30 |
| Sumitomo Chemical Industry | High-purity Alumina AKS-G | 0.05 | 86.80 | 23.10 |
| Sumitomo Chemical Industry | High-purity Alumina AKP-GM | 0.05 | 89.60 | 41.60 |
| Sumitomo Chemical Industry | High-purity Alumina AKP-HP | 0.45 | 69.80 | 81.90 |
| Sumitomo Chemical Industry | High-purity Alumina CAH-G00 | 5.00 | 91.90 | 69.10 |
| Sumitomo Chemical Industry | Hardened-type Alumina BK-103 | 2.20 | 87.00 | 68.10 |
| Sumitomo Chemical Industry | Lτ-5 *4 | 0.41 | 84.90 | 64.10 |
| Showa Denko | HIGILITE H-43M *5 | 0.73 | 87.40 | 63.80 |
| Showa Denko | HIGILITE H-32ST *5 | 2.50 | 90.30 | 58.00 |
| Showa Denko | HIGILITE H-42S *5 | 0.90 | 88.90 | 69.60 |
| Showa Denko | HIGILITE H-43S *5 | 0.75 | 87.50 | 64.80 |
| Showa Denko | Fine Particulate Low-Soda Alumina AL-43PCA | 5.20 | 86.60 | 44.40 |
| Wako Pure Chemical | Special Grade Zinc White | 0.40 | 64.80 | 82.10 |
| Sumitomo Cement | Ultra-fine Zinc Oxide | 0.04 | 71.35 | 70.65 |
| Ishihara Sangyo | Taipeke A-100 *6 | 0.15 | 20.70 | 85.35 |
| Sumitomo Metal | Unidispersion Titania *6 | 0.50 | 54.50 | 83.30 |
| Sumitomo Chemical Industry | Luxerene Silk H *6 | 2-20 | 66.00 | 56.70 |
| Toray | Nylone Powder | 5.00 | 91.70 | 57.20 |
|  | Powder prepared in Example 1 | 5.3 | 88.00 | 72.50 |

*1 Silica
*2 Sericite
*3 Baruim sulfate
*4 $LiAlO_3$
*5 Aluminum hydroxide
*6 $TiO_2$ Table 2 demonstrates that the pigment prepared in Example 1 of the present invention possessed greater scattering transmittance and total transmittance than any other commercially available pigments, thus evidencing its high transparency and distinctness-inhibition effect.

EXAMPLE 15

| Component | Composition (%) |
|---|---|
| (1) Mica | Balance |
| (2) Powder prepared in Example 1 | 50 |
| (3) Talc | 20 |
| (4) Titanium oxide | 10 |
| (5) Red iron oxide | 0.8 |
| (6) Yellow iron oxide | 2.5 |
| (7) Black iron oxide | 0.1 |
| (8) Liquid paraffin | 8 |
| (9) Bees wax | 2 |
| (10) Preservative | q.s. |
| (11) perfume | small amount |
| Total | 100 |

Method of preparation

The above components (1)–(7) were mixed and pulverized. The mixture was charged into a high speed blender and components (8)–(10), mixed and dissolved at 80° C. in advance, were added to it and homogeneously blended. After the addition of components (11), the mixture was again pulverized and sieved. The resulting mixture was charged into a metallic pan to compress mold it.

EXAMPLE 16

A powder foundation was prepared in the same manner as in Example 1, except that instead of component (20) the powder prepared in Example 2 was used.

| Component | Composition (%) |
|---|---|
| (1) Mica | Balance |
| (2) Commercial barium sulfate *1 | 50 |
| (3) Talc | 20 |
| (4) Titanium oxide | 10 |
| (5) Red iron oxide | 0.8 |
| (6) Yellow iron oxide | 2.5 |
| (7) Black iron oxide | 0.1 |
| (8) Liquid paraffin | 8 |
| (9) Bees wax | 2 |
| (10) Preservative | q.s. |
| (11) perfume | small amount |
| Total | 100 |

*1: Plate-like barium sulfate H (manufacture by Sakai Chemical Industry, Ltd., average diameter: 6.3 μm, irregular plate-like crystals)

Method of preparation

The above components (1)–(7) were mixed and pulverized. The mixture was charged into a high speed blender and components (8)–(10), mixed and dissolved at 80° C. in advance, were added to it and homogeneously blended. After the addition of components (11), the mixture was again pulverized and sieved. The resulting mixture was charged into a metallic pan to compress mold it.

COMPARATIVE EXAMPLE 9

| Component | Composition (%) |
|---|---|
| (1) Mica | Balance |
| (2) Nylon powder | 10 |
| (3) Talc | 20 |
| (4) Titanium oxide | 10 |
| (5) Red iron oxide | 0.8 |
| (6) Yellow iron oxide | 2.5 |
| (7) Black iron oxide | 0.1 |
| (8) Liquid paraffin | 8 |
| (9) Bees wax | 2 |
| (10) Preservative | q.s. |
| (11) Perfume | small amount |
| Total | 100 |

Method of preparation

The above components (1)–(7) were mixed and pulverized. The mixture was charged into a high speed blender and components (8)–(10), mixed and dissolved at 80° C. in advance, were added to it and homogeneously blended. After the addition of components (11), the mixture was again pulverized and sieved. The resulting mixture was charged into a metallic pan to compress mold it.

TEST EXAMPLE 2

Evaluation was performed by 14 expert panelists on the powder foundations of Examples 15–16 and Comparative Examples 8–9 with respect to the following items according to the standard described below. The results are shown in Table 3.

Evaluation Items (1) Effect of hiding spots and freckles
(2) Fineness of texture
(3) Naked skin feeling
(4) Covering effect

Evaluation Standard

Samples of Examples 8 and 9 or Comparative Examples 15 and 16 which were evaluated better than samples of Comparative Examples 15 and 16 or Examples 8 and 9 were rated 2 points. If the evaluation results was slightly better than the other, the samples were rated 1 point. If the panelist could not tell which was better, no point was give to the sample.

TABLE 3

| Sample | Evaluation Item | | | |
|---|---|---|---|---|
| | (1) | (2) | (3) | (4) |
| Comparative Example 8 | 2 | 2 | 3 | 5 |
| Comparative Example 9 | 1 | 2 | 5 | 4 |
| Example 15 | 10 | 9 | 8 | 8 |
| Example 16 | 10 | 9 | 8 | 8 |

The results shown in Table 3 confirms that when applied to the skin the cosmetics of the present invention effectively hide freckles, spots, and the like due to the distinctness-inhibiting effects of barium sulfate which was incorporated in the cosmetics. Furthermore, the improvements were seen in the fineness of the texture which represents a delicate feeling to the touch to the skin. The cosmetics of the present invention further satisfied both the fine naked skin feeling and the skin covering effect, at the same time, which have been required but not satisfied by the conventional cosmetic compositions.

EXAMPLE 17

| Component | Composition (%) |
|---|---|
| (1) Mica | Balance |
| (2) Powder prepared in Example 1 | 50 |
| (3) Talc | 20 |
| (4) Titanium oxide | 0.5 |
| (5) Red iron oxide | 0.1 |
| (6) Yellow iron oxide | 0.1 |
| (7) Black iron oxide | 0.01 |
| (8) Liquid paraffin | 8 |
| (9) Bees wax | 2 |
| (10) Preservative | q.s. |
| (11) perfume | small amount |
| Total | 100 |

Method of preparation

The above components (1)–(7) were mixed and pulverized. The mixture was charged into a high speed blender and components (8)–(10), mixed and dissolved at 80° C. in advance, were added to it and homogeneously blended. After the addition of components (11), the mixture was again pulverized and sieved. The resulting mixture was charged into a metallic pan to compress mold it.

EXAMPLE 18

| Component | Composition (%) |
|---|---|
| (1) Mica | Balance |
| (2) Powder prepared in Example 1 | 50 |
| (3) Talc | 20 |
| (4) Titanium oxide | 0.5 |
| (5) Red iron oxide | 0.1 |
| (6) Yellow iron oxide | 0.1 |
| (7) Black iron oxide | 0.01 |
| (8) Magnesium stearate | 10 |
| (9) Preservative | q.s. |
| (10) Perfume | small amount |
| Total | 100 |

Method of preparation

The above components (1)–(8) were mixed and pulverized. The mixture was charged into a high speed blender and components (9)–(10), mixed and dissolved at 80° C. in advance, were added to it and homogeneously blended. The mixture was again pulverized and sieved.

EXAMPLE 19

| Component | Composition (%) |
|---|---|
| (1) Stearic acid | 5.5 |
| (2) Oleophylic monostearyl glycerol | 2.5 |
| (3) Cetostearyl alcohol | 1 |
| (4) Monolauryl propyleneglycol | 3 |
| (5) Squalan | 7 |
| (6) Olive oil | 8 |
| (7) Purified water | Balance |
| (8) Preservative | q.s. |
| (9) Triethanolamine | 1.2 |
| (10) Sorbit | 3 |
| (11) Titanium oxide | 10 |
| (12) Talc | 5 |
| (13) Pigment (Black iron oxide, red iron oxide, yellow iron oxide) | q.s. |
| (14) Powder prepared in Example 1 | 8 |
| (15) Perfume | Small amount |
| Total | 100 |

Method of preparation

The above pigment components (11)–(14) were mixed and pulverized. The mixture was added to and dispersed in the solution of water phase components (7)–(10), which had been separately prepared, and heated at 75° C. The oil phase components (1)–(6), heated at 80° C. to dissolution, were added to the water phase mixture with stirring. The mixture was cooled while stirring, and component (15) was added at a temperature of 50° C. The stirring was continued to further cool the mixture and to obtain a cream product.

EXAMPLE 20

| Component | Composition (%) |
|---|---|
| (1) Mica | Balance |
| (2) Powder prepared in Example 2 | 50 |
| (3) Talc | 20 |
| (4) Titanium oxide | 4 |
| (5) Zinc stearate | 5 |
| (6) Rice starch | 5 |
| (7) Coloring agent | 3 |
| (8) Liquid paraffin | 3 |
| (9) Preservative | q.s. |
| (10) Perfume | Small amount |
| Total | 100 |

Method of preparation

The above components (1)–(7) were mixed to develop color. Components (8)–(10) were sprayed to the colored mixture in a mixer and homogeneously blended. After sieving, the mixture was press molded in a metallic pan.

EXAMPLE 21

| Component | Composition (%) |
|---|---|
| (1) Mica | Balance |
| (2) Powder prepared in Example 1 | 50 |
| (3) Talc | 5 |
| (4) Titanium mica | 5 |
| (5) Zinc stearate | 5 |
| (6) Zinc laurate | 3 |
| (7) Pigment (Black iron oxide, red iron oxide, yellow iron oxide) | 10 |
| (8) Liquid paraffin | 7.5 |
| (9) Preservative | q.s. |
| (10) Perfume | Small amount |
| Total | 100 |

Method of preparation

The above components (1)–(7) were mixed to develop color. Components (8)–(10) were sprayed to the colored mixture in a mixer and homogeneously blended. After sieving, the mixture was press molded in a metallic pan.

EXAMPLE 22

| | Composition | |
|---|---|---|
| | Component | (%) |
| (1) | Tiatanium oxide | 1 |
| (2) | Lithol rubine B (CI No. 15850) | 1 |
| (3) | Lithol rubine BCA (CI No. 15850) | 2 |
| (4) | Tartrazine (CI No. 19140) | 1 |
| (5) | Tetrabromofluorescein (CI No. 45380) | 0.1 |
| (6) | Powder prepared in Example 3 | 5 |
| (7) | Castor oil | 46.9 |
| (8) | Octyl dodecanol | 15 |
| (9) | Lanolin | 5 |
| (10) | Liquid lanolin | 5 |
| (11) | Bees wax | 5 |
| (12) | Ozokelite | 4 |
| (13) | Candelilla wax | 7 |
| (14) | Carnauba wax | 1 |
| (15) | Antioxidant | q.s. |
| (16) | Preservative | q.s. |
| (17) | Perfume | Small amount |
| | Total | 100 |

Method of preparation

The above components (7)–(14) were mixed and heated to homogeneously dissolve. To this mixture components (1)–(6) were added and kneaded by a roll mill to disperse homogeneously. After dissolution again, components (15)–(17) were added. The mixture was then defoamed, charged to a mold, and quenched to solidify. The solid product was released from the mold, packed in the container. After shaping, the stick was flamed to make its surface uniform.

EXAMPLE 23

| | Composition | |
|---|---|---|
| | Component | (%) |
| (1) | Carnauba wax | 5 |
| (2) | Bees wax | 1 |
| (3) | Microcrystalline wax | 10 |
| (4) | White petrolatum | 1 |
| (5) | Light liquid iso-paraffin | 67.5 |
| (6) | Organic bentonite | 0.5 |
| (7) | Powder prepared in Example 4 | 10 |
| (8) | Titanium oxide | 3 |
| (9) | Carbon black | 2 |
| (10) | Preservative | q.s. |
| | Total | 100 |

Method of preparation

Component (6) was added to a portion of component (5) and dispersed by a colloidal mill to gelatin. Components (7)–(9) were added to a mixture of components (1)–(4) and (10) which had been mixed and heated to dissolution in advance. After cooling, the mixture was kneaded by a roll mill and heated again. To this the above bentonite gell and the remaining portion of component (5) were added and cooled with stirring.

EXAMPLE 24

| | Composition | |
|---|---|---|
| | Component | (%) |
| (1) | Bees wax | 5.5 |
| (2) | Cetanol | 4.5 |

-continued

| | Composition | |
|---|---|---|
| | Component | (%) |
| (3) | Hydrogenated lanolin | 7 |
| (4) | Squalan | 33 |
| (5) | Fatty acid glycerol | 3.5 |
| (6) | Oleophylic monostearyl glycerol | 2 |
| (7) | POE (20) sorbitan-monolauric acid ester | 2 |
| (8) | Powder prepared in Example 6 | 8 |
| (9) | Perfume | 0.1 |
| (10) | Preservative | 0.2 |
| (11) | Antioxidant | 0.1 |
| (12) | Propylene glycol | 10 |
| (13) | Purified water | Balance |
| | Total | 100 |

Method of preparation

The water phase components (8), (10), (12), and (13) were mixed with stirring. Other components were heated at 80° C. to dissolution. The above mixture of water phase components was added to the oil phase to effect pre-emulsification, followed by complete emulsification by a homogenizer. The emulsion was cooled to 30° C. to obtain the product.

EXAMPLE 25

| | Composition | |
|---|---|---|
| | Component | (%) |
| (1) | Mica | Balance |
| (2) | Powder prepared in Example 1 | 40 |
| (3) | Polymethylmethacrylate (PMMA) with an average volumetric accumulative particle diameter of 0.4 μm | 10 |
| (4) | Talc | 20 |
| (5) | Titanium oxide | 10 |
| (6) | Red iron oxide | 0.8 |
| (7) | Yellow iron oxide | 2.5 |
| (8) | Black iron oxide | 0.1 |
| (9) | Liquid paraffin | 8 |
| (10) | Bees wax | 2 |
| (11) | Preservative | q.s. |
| (12) | Perfume | Small amount |
| | Total | 100 |

Method of preparation

The above components (1)–(8) were mixed and pulverized. The mixture was charged into a high speed blender and components (9)–(11), mixed and dissolved at 80° C. in advance, were added to it and homogeneously blended. After the addition of components (12), the mixture was again pulverized and sieved. The resulting mixture was charged into a metallic pan to compress mold it.

EXAMPLE 26

A powder foundation was prepared in the same manner as in Example 25, except that instead of component (3) of Example 25 a spherical silica-containing composite oxide (a spherical ceramic manufactured by Tokuyama Soda Co., Ltd.) with an average volumetric accumulative particle diameter of 0.1 μm was used.

COMPARATIVE EXAMPLE 10

| | Composition | |
|---|---|---|
| | Component | (%) |
| (1) | Mica | Balance |

-continued

| | Composition | |
|---|---|---|
| | Component | (%) |
| (2) | Commercial plate-like barium sulfate *1 | 40 |
| (3) | Polymethylmethacrylate (PMMA) with an average volumetric accumulative particle diameter of 0.4 μm | 10 |
| (4) | Talc | 20 |
| (5) | Titanium oxide | 10 |
| (6) | Red iron oxide | 0.8 |
| (7) | Yellow iron oxide | 2.5 |
| (8) | Black iron oxide | 0.1 |
| (9) | Liquid paraffin | 8 |
| (10) | Bees wax | 2 |
| (11) | Preservative | q.s. |
| (12) | Perfume | Small amount |
| | Total | 100 |

*1: Plate-like barium sulfate H (manufacture by Sakai Chemical Industry, Ltd., average diameter: 6.3 μm, irregular plate-like crystals)

Method of preparation

The above components (1)–(8) were mixed and pulverized. The mixture was charged into a high speed blender and components (9)–(11), mixed and dissolved at 80° C. in advance, were added to it and homogeneously blended. After the addition of components (12), the mixture was again pulverized and sieved. The resulting mixture was charged into a metallic pan to compress mold it.

COMPARATIVE EXAMPLE 11

| | Composition | |
|---|---|---|
| | Component | (%) |
| (1) | Mica | Balance |
| (2) | Powder prepared in Example 1 | 40 |
| (3) | Nylon powder | 10 |
| (4) | Talc | 20 |
| (5) | Titanium oxide | 10 |
| (6) | Red iron oxide | 0.8 |
| (7) | Yellow iron oxide | 2.5 |
| (8) | Black iron oxide | 0.1 |
| (9) | Liquid paraffin | 8 |
| (10) | Bees wax | 2 |
| (11) | Preservative | q.s. |
| (12) | Perfume | small amount |
| | Total | 100 |

Method of preparation

The above components (1)–(8) were mixed and pulverized. The mixture was charged into a high speed blender and components (9)–(11), mixed and dissolved at 80° C. in advance, were added to it and homogeneously blended. After the addition of components (12), the mixture was again pulverized and sieved. The resulting mixture was charged into a metallic pan to compress mold it.

COMPARATIVE EXAMPLE 12

| | Composition | |
|---|---|---|
| | Component | (%) |
| (1) | Mica | Balance |
| (2) | Powder prepared in Example 1 | 50 |
| (3) | Talc | 20 |
| (4) | Titanium oxide | 0.5 |
| (5) | Red iron oxide | 0.8 |
| (6) | Yellow iron oxide | 2.5 |
| (7) | Black iron oxide | 0.1 |

-continued

| | Composition | |
|---|---|---|
| | Component | (%) |
| (8) | Liquid paraffin | 8 |
| (9) | Bees wax | 2 |
| (10) | Preservative | q.s. |
| (11) | Perfume | Small Amount |
| | Total | 100 |

Method of preparation

The above components (1)–(7) were mixed and pulverized. The mixture was charged into a high speed blender and components (8)–(10), mixed and dissolved at 80° in advance, were added to it and homogeneously blended. After the addition of components (11), the mixture was again pulverized and sieved. The resulting mixture was charged into a metallic pan to compress mold it.

TEST EXAMPLE 3

Evaluation was performed by 14 expert panelists on the powder foundations of Examples 25-26 and Comparative Examples 10-11 with respect to the following items according to the standard described below. The results are shown in Table 3.

Evaluation Items (1) Effect of hiding spots and freckles
(2) Fineness of texture
(3) Naked skin feeling
(4) Covering effect Evaluation Standard 2: Good
1: Better
0: Cannot decide

TABLE 4

| Sample | Evaluation Item | | | |
|---|---|---|---|---|
| | (1) | (2) | (3) | (4) |
| Comparative Example 10 | 2 | 2 | 3 | 4 |
| Comparative Example 11 | 1 | 2 | 5 | 3 |
| Example 25 | 9 | 10 | 9 | 7 |
| Example 26 | 9 | 8 | 9 | 7 |

The results shown in Table 4 confirms that when applied to the skin the cosmetics of the present invention effectively hide freckles, spots, and the like tue to the distinctness-inhibiting effects of barium sulfate which was incorporated in the cosmetics. Furthermore, the improvements were seen in the fineness of the texture which represents a delicate feeling to the touch to the skin. The cosmetics of the present invention further satisfied both the fine naked skin feeling and the skin covering effect, at the same time, which have been required but not satisfied by the conventional cosmetic compositions.

TEST EXAMPLE 4

Evaluation was performed by 10 expert panelists on the powder foundations of Examples 25-26 and Comparative Examples 11-12 with respect to the extendibility over the skin and adherence to the skin. The results are shown in Table 5.

Evaluation Standard

AAA: 8-10 panelists responded favorably
BBB: 5-7 panelists responded favorably
CCC: 0-4 panelists responded favorably

TABLE 5

| Test Samples | Extendibility | Adherence |
|---|---|---|
| Powder foundation of Example 25 | AAA | AAA |
| Powder foundation of Example 26 | AAA | AAA |
| Powder foundation of Comparative Example 11 | AAA | CCC |
| Powder foundation of Comparative Example 12 | BBB | AAA |

TEST EXAMPLE 5

Relative friction coefficient was measured on the powder foundations of Examples 25-26 and Comparative Example 12 using a surface tester, Heidon 14 (trademark, manufactured by Sintoyo Science Co.). A prescribed amount of test powder foundations was coated over a sheet of pig skin. The relative friction coefficient of a sample was determined as the ratio of the friction coefficient measured on the pig skin over which the sample was coated and the friction coefficient of the non-coated pig skin. The results are given in Table 6.

TABLE 6

| Test Samples | Relative friction coefficient |
|---|---|
| Powder foundation of Example 25 | 1.1 |
| Powder foundation of Example 26 | 1.2 |
| Powder foundation of Comparative Example 12 | 2.0 |

The results given in Tables 5 and 6 demonstrate superior extendibility over the skin and adherence to the skin of the cosmetics of the present invention.

EXAMPLE 27

| | Component | Composition (%) |
|---|---|---|
| (1) | Mica | Balance |
| (2) | Powder prepared in Example 1 | 35 |
| (3) | Spherical silica with an average volumetric accumulative particle diameter of 0.5 μm | 15 |
| (4) | Talc | 20 |
| (5) | Titanium oxide | 0.5 |
| (6) | Red iron oxide | 0.1 |
| (7) | Yellow iron oxide | 0.1 |
| (8) | Black iron oxide | 0.01 |
| (9) | Liquid paraffin | 8 |
| (10) | Bees wax | 2 |
| (11) | Preservative | q.s. |
| (12) | Perfume | Small amount |
| | Total | 100 |

Method of preparation

The above components (1)-(8) were mixed and pulverized. The mixture was charged into a high speed blender and components (9)-(11), mixed and dissolved at 80° C. in advance, were added to it and homogeneously blended. After the addition of components (12), the mixture was again pulverized and sieved. The resulting mixture was charged into a metallic pan to compress mold it.

EXAMPLE 28

| | Component | Composition (%) |
|---|---|---|
| (1) | Mica | Balance |
| (2) | Powder prepared in Example 1 | 30 |
| (3) | Spherical PMMA with an average volumetric accumulative particle diameter of 0.8 μm | 20 |
| (4) | Talc | 20 |
| (5) | Titanium oxide | 0.5 |
| (6) | Red iron oxide | 0.1 |
| (7) | Yellow iron oxide | 0.1 |
| (8) | Black iron oxide | 0.01 |
| (9) | Magnesium stearate | 10 |
| (10) | Preservative | q.s. |
| (11) | Perfume | Small amount |
| | Total | 100 |

Method of preparation

The above components (1)-(9) were mixed and pulverized. The mixture was charged into a high speed blender and components (10)-(11), mixed and dissolved at 80° C. in advance, were added to it and homogeneously blended. The mixture was again pulverized and sieved.

Example 29

| | Component | Composition (%) |
|---|---|---|
| (1) | Mica | Balance |
| (2) | Powder prepared in Example 2 | 45 |
| (3) | Spherical PMMA with an average volumetric accumulative particle diameter of 0.4 μm | 5 |
| (4) | Talc | 20 |
| (5) | Titanium oxide | 4 |
| (6) | Red iron oxide | 5 |
| (7) | Yellow iron oxide | 5 |
| (8) | Black iron oxide | 3 |
| (9) | Magnesium stearate | .3 |
| (10) | Preservative | q.s. |
| (11) | Perfume | Small amount |
| | Total | 100 |

Method of preparation

The above components (1)-(8) were mixed to develop color. Components (9)-(11) were sprayed to the colored mixture in a mixer and homogeneously blended. After sieving, the mixture was press molded in a metallic pan.

EXAMPLE 30

| | Component | Composition (%) |
|---|---|---|
| (1) | Mica | Balance |
| (2) | Powder prepared in Example 1 | 45 |
| (3) | Spherical silica-containing composite oxide with an average volumetric accumulative particle diameter of 0.1 μm | 5 |
| (4) | Talc | 5 |
| (5) | Titanium mica | 5 |
| (6) | Zinc stearate | 5 |

| Composition | | |
|---|---|---|
| Component | | (%) |
| (7) | Zinc laurate | 3 |
| (8) | Pigment<br>(Black iron oxide, red iron oxide, yellow iron oxide) | 10 |
| (9) | Liquid paraffin | 7.5 |
| (10) | Preservative | q.s. |
| (11) | Perfume | Small amount |
| | Total | 100 |

Method of preparation

The above components (1)–(8) were mixed to develop color. Components (9)–(11) were sprayed to the colored mixture in a mixer and homogeneously blended. After sieving, the mixture was press molded in a metallic pan.

PREPARATION EXAMPLE 1

Preparation of zinc salt of sodium momocetyl phosphate.

Into a 500 ml separable flask (hereinafter referred to as "reaction vessel") were charged 50 gm of monocetyl phosphoric acid and 100 gm of ethanol. To the mixture was added a solution of 6.29 gm of 96% sodium hydroxide in 200 gm of ion-exchanged water. The mixture was heated to 80° C. and, after confirming the dissolution of the components to transparency, was stirred for a further 30 minutes. A solution of 22.3 gm of $ZnSO_4 \cdot 7H_2O$ in 100 gm of ion-exchanged water was added dropwise to effect the salt exchange. After the completion of the addition, the mixture was stirred for 30 minutes. 8.70 gm of 33.33% aqueous solution sodium hydroxide was administered to adjust the pH of the solution to 3. The mixture was stirred for a further 1 hour to terminate the reaction, followed by cooling, filtration, washing with water, and drying to obtain 50.3 gm of zinc salt of sodium monocetyl phosphate.

Zinc salt of sodium monocetyl phosphate thus prepared had an average particle size of 14 μm, and the crystal plate had a ratio of the thickness and the larger diameter of 1:1.25 and a ratio of the thickness and the larger diameter of 1:10.

PREPARATION EXAMPLE 2

Preparation of Calcium N-Lauroyltaurine

Into a 1 liter four-necked flask equipped with a stirrer, a dropping funnel, and a thermometer were charged over 15 minutes 20 gm of sodium N-lauroyltaurine and 380 gm of ion-exchanged water. The mixture was heated to 40° C. while stirring. 135 gm of 5% aqueous solution of calcium chloride was administered from the dropping funnel, while confirming deposition of calcium N-lauroyltaurine crystals. After the completion of the addition, the mixture was stirred for 1 hour at 40° C. to complete the salt exchange. The resulting reaction mixture was allowed to cool to room temperature, filtered, washed with water, and dried to obtain 19.4 gm of white crystals of calcium N-lauroyltaurine (yield: 98.9%).

Calcium N-lauroyltaurine thus prepared had an average particle size of 7.4 μm, smaller and larger diameters of the ratio 1:1.5 and the ratio of thickness and larger diameter of 1:20.

PREPARATION EXAMPLE 2

Preparation of calcium salt of N-lauroyl-β-alanine

Into a 1 liter four-necked flask equipped with a stirrer, a dropping funnel, and a thermometer were charged 50 gm of N-lauroyl-β-alanine, 7.4 gm sodium hydroxide, and 423 gm of ion-exchanged water. The mixture was heated to 60° C. while stirring. 64.7 gm of 20% aqueous solution of calcium chloride was administered from the dropping funnel over 2 hours, while confirming deposition of calcium N-lauroyl-β-alanine crystals. After the completion of the addition, the mixture was stirred for 1 hour at 60° C. to complete the salt exchange. The resulting reaction mixture was allowed to cool to room temperature, filtered, washed with water, and dried at room temperature to obtain 52.7 gm of white crystals of the target calcium N-lauroyl-β-alanine (yield: 98.5%).

Calcium N-lauroyl-β-alanine thus prepared had an average particle size of 11.3 βm, a ratio of the smaller and larger diameters of 1:1.5 and a ratio of the thickness and the larger diameter of 1:10.

EXAMPLE 31

Powder foundations having the compositions listed in Table 7 were prepared and were organoleptically evaluated. The results are shown in Table 7.

Method of Preparation

Components (1)–(9) were mixed and pulverized, and charged into in a Henshel mixer to effect thorough stirring, while slowly adding components (10) and (11). The bulk thus obtained was filled into metallic pans to obtain foundations.

Method of Evaluation

The organoleptic evaluation was carried out by 10 expert panelist according to the following standard.

| (1) | Softness upon use | |
|---|---|---|
| | Very soft | 5 |
| | Soft | 4 |
| | Can not tell | 3 |
| | Not very soft | 2 |
| | Not soft | 1 |
| (2) | Fitness with the skin | |
| | Very good | 5 |
| | Good | 4 |
| | Can not tell | 3 |
| | Not good | 2 |
| | Bad | 1 |
| (3) | Extendibility and smoothness | |
| | Very smooth | 5 |
| | Smooth | 4 |
| | Can not tell | 3 |
| | Not very smooth | 2 |
| | Not smooth | 1 |
| (4) | Freshness | |
| | Very fresh | 5 |
| | Fresh | 4 |
| | Can not tell | 3 |
| | Not so fresh | 2 |
| | Not fresh | 1 |
| (5) | Thicklessness | |
| | Not thick at all | 5 |
| | Not thick | 4 |
| | Can not tell | 3 |
| | Slightly thick | 2 |
| | Thick | 1 |
| (6) | Effect of hiding freckles and spots | |
| | Excellent | 5 |
| | Good | 4 |
| | Normal | 3 |

|  | -continued |
|---|---|
| Not good | 2 |
| Bad | 1 |

TABLE 7

|  | Invention Product | | | Comparative Product | | |
|---|---|---|---|---|---|---|
|  | 1 | 2 | 3 | 1 | 2 | 3 |
| Component (%) | | | | | | |
| (1) Plate-like barium sulfate | 40 | 40 | 40 | 40 | — | — |
| (2) Zinc salt of sodium monocetyl phosphate prepared in Preparation Example 1 | 30 | 10 | — | — | 30 | 30 |
| (3) Calcium N-lauroyltaurine prepared in Preparation Example 2 | — | 20 | — | — | — | — |
| (4) Calcium N-lauroyl-$\beta$-alanine prepared in Preparation Example 3 | — | — | 30 | — | — | — |
| (5) Press-aid* | 10 | 10 | 10 | 15 | 10 | 10 |
| (6) Sericite | Balnce | Balnce | Balnce | Balnce | Balnce | Balnce |
| (7) Nylon powder | 5 | 5 | — | 10 | 5 | 5 |
| (8) Titanium oxide | 5 | 5 | 5 | 5 | 5 | 15 |
| (9) Iron oxide | 2 | 2 | 2 | 2 | 2 | 2 |
| (10) Silicone oil | 3 | 3 | 3 | 3 | 3 | 3 |
| (11) Perfume | 0.1 | 0.1 | 0.1 | 0.1 | 0.1 | 0.1 |
| Total | 100 | 100 | 100 | 100 | 100 | 100 |
| Evaluation item | | | | | | |
| (1) Softness upon use | 5 | 5 | 5 | 1 | 5 | 5 |
| (2) Fitness with the skin | 5 | 5 | 5 | 3 | 5 | 5 |
| (3) Extendibility and smoothness | 5 | 4 | 4 | 3 | 5 | 5 |
| (4) Freshness | 4 | 5 | 4 | 3 | 4 | 4 |
| (5) Thicklessness | 5 | 5 | 5 | 5 | 5 | 1 |
| (6) Effect of hiding freckles and spots | 5 | 5 | 5 | 5 | 1 | 5 |

*Trademark, synthetic hydrocarbon wax, manufactured by Pressperse Inc.)

EXAMPLE 32

| Component | Composition (%) |
|---|---|
| (1) Powder prepared in Example 1 | 20 |
| (2) Zinc salt of sodium monocetyl phosphate prepared in Preparation Example 1 | 20 |
| (3) Amihope (Product of Ajinomoto Co.) | 20 |
| (4) Talc | Balance |
| (5) Sericite | 15 |
| (6) Titanium oxide | 2 |
| (7) Iron oxide | 1 |
| (8) Squalan | 2 |
| (9) Silicone oil | 2 |
| (10) Perfume | 0.1 |
| Total | 100 |

Method of preparation

The above components (1)–(7) were mixed and pulverized. The mixture was charged into a Henshel mixer and thoroughly stirred, while components (8)–(10) were slowly added. The bulk thus obtained was filled in metallic pans to produce cake foundations.

EXAMPLE 33

| Component | Composition (%) |
|---|---|
| (1) Powder prepared in Example 1 | 60 |
| (2) Calcium N-lauroyltaurine prepared in Preparation Example 2 | Balance |
| (3) Titanium oxide | 2 |
| (4) Iron oxide | 1 |
| (5) Squalan | 1 |
| (6) Perfume | 0.1 |
| Total | 100 |

Method of preparation

The above components (1)–(4) were mixed and pulverized. The mixture was charged into a Henshel mixer and thoroughly stirred, while components (5)–(6) were slowly added. The bulk thus obtained was filled in metallic pans to produce powder foundations.

EXAMPLE 34

| Component | Composition (%) |
|---|---|
| (1) Powder prepared in Example 1 | 20 |
| (2) Calcium N-lauroyltaurine prepared in Preparation Example 2 | Balance |
| (3) Press-aid (Trademark, manufactured by Pressperse Inc.) | 20 |
| (4) Titanium oxide | 5 |
| (5) Coloring agent | 5 |
| (6) Perfume | 0.1 |
| Total | 100 |

Method of Preparation

The above components (1)–(5) were mixed and pulverized. The mixture was charged into a Henshel mixer and thoroughly stirred, while component (6) was slowly added. The bulk thus obtained was filled in metallic pans to produce rouge.

EXAMPLE 35

| Component | Composition (%) |
|---|---|
| (1) Powder prepared in Example 1 | 30 |
| (2) Calcium N-lauroyl-$\beta$-alanine prepared in Preparation Example 3 | 30 |

-continued

| | Component | Composition (%) |
|---|---|---|
| (3) | Press-aid (Trademark, manufactured by Pressperse Inc.) | 20 |
| (4) | Talc | Balance |
| (5) | Titanium oxide | 5 |
| (6) | Coloring agent | 15 |
| | Total | 100 |

Method of Preparation

The above components (1)-(6) were mixed and pulverized. The bulk thus obtained was filled in metallic pans to produce powder eye-shadow.

Barium sulfate having a plate-like structure of the present invention possesses high light scattering and transparent characteristics. The cosmetic compositions to which the barium sulfate is incorporated exhibits excellent extendibility and adhesion to the skin and can effectively hide the spots or freckles on the skin. Furthermore, the cosmetic composition satisfies both the fine naked skin feeling and the skin covering effect, which have never been satisfied by conventional cosmetic compositions.

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing barium sulfate having a plate crystal structure of which the aspect ratio is 5–100 and the ratio of the square of the circumference of the plate and the area of the orthogonal projection plane is 20:1–150:1, comprising reacting a solution of a barium salt having a barium ion concentration of 0.001–0.05 mole/l and a solution of a sulfate having a sulfate ion concentration of 0.001–0.05 mole/l at a ratio of 1:10–5:1, at a pH of 1.0–5.0, and at a temperature of 50–100° C.

* * * * *